(12) United States Patent
Ye et al.

(10) Patent No.: US 8,722,634 B2
(45) Date of Patent: May 13, 2014

(54) **USE OF COMPOUNDS EXTRACTED FROM *MOMORDICA CHARANTIA* L. IN THE MANUFACTURE OF MEDICAMENTS FOR PREVENTION AND TREATMENT OF DIABETES AND OBESITY**

(75) Inventors: Yang Ye, Shanghai (CN); Minjia Tan, Shanghai (CN); Changqiang Ke, Shanghai (CN); Tong Chen, Shanghai (CN); Xiqiang Li, Shanghai (CN); Edward Kraegen, Sydney (AU); Jiming Ye, Sydney (AU); David James, Sydney (AU); Gregory Cooney, Sydney (AU)

(73) Assignees: Shanghai Institute of Materia Medica, Chinese Academy of Sciences, Shanghai (CN); The Garvan Institute of Medical Research, Australia, Sydney (AU)

( * ) Notice: Subject to any disclaimer, the term of this patent is extended or adjusted under 35 U.S.C. 154(b) by 13 days.

(21) Appl. No.: 12/865,843

(22) PCT Filed: Jan. 14, 2009

(86) PCT No.: PCT/CN2009/000050
§ 371 (c)(1),
(2), (4) Date: Dec. 3, 2010

(87) PCT Pub. No.: WO2009/097735
PCT Pub. Date: Aug. 13, 2009

(65) Prior Publication Data
US 2011/0152208 A1    Jun. 23, 2011

(30) Foreign Application Priority Data
Jan. 31, 2008  (CN) .......................... 2008 1 0033348

(51) Int. Cl.
*A61K 31/70*    (2006.01)
(52) U.S. Cl.
USPC .......................................................... 514/26
(58) Field of Classification Search
USPC .......................................... 514/26, 177, 179
See application file for complete search history.

(56) References Cited

PUBLICATIONS

Harinantenaina et al., "*Momordica charantia* Constituents and Antidiabetic Screening of the Isolated Major Compounds," Chem. Pharm. Bull., vol. 54, No. 7, pp. 1017-1021 (Jul. 2006).
Zhang et al., "Modern Research Progress of Bittermelon," Food and Drug (Chinese), vol. 8, No. 4, pp. 26-30 (Non-English Article with English Abstract) (2006).
Li et al., "The Research Progress on Momordicoside," Food Research and Development (Chinese), vol. 26, No. 3, pp. 21-24 (Non-English Article with English Abstract) (Jun. 2005).

*Primary Examiner* — Elli Peselev
(74) *Attorney, Agent, or Firm* — Baker & Hostetler LLP

(57) ABSTRACT

The present invention disclosed a medical use of cucurbitane triterpenoids represented by the following formula and isolated from *Momordica charantia* L. of Cucurbitaceae family in the preparation of medications for prevention and treatment of diabetes and obesity. The above cucurbitane triterpenoids may be acted as a glucose uptake stimulator, an agonist for the translocation of glucose transporter 4 (GLUT4) to the cell membrane, and an activator of adenosine monophosphate-activated protein kinase (AMPK). They may have potential for the prevention and treatment of diabetes and obesity.

6 Claims, 3 Drawing Sheets

▲: trihydroxycucurbita-5,23(E)-dien-19-al

✳: 22(S),23(R),24(R),25-tetrahydroxycucurbita-5-ene

▲ : trihydroxycucurbita-5,23(E)-dien-19-al

✳ : 22(S),23(R),24(R),25-tetrahydroxycucurbita-5-ene

▲ : trihydroxycucurbita-5,23(E)-dien-19-al

✳ : 22(S),23(R),24(R),25-tetrahydroxycucurbita-5-ene

USE OF COMPOUNDS EXTRACTED FROM *MOMORDICA CHARANTIA* L. IN THE MANUFACTURE OF MEDICAMENTS FOR PREVENTION AND TREATMENT OF DIABETES AND OBESITY

CROSS-REFERENCE TO RELATED APPLICATIONS

This application is a National Stage of International Patent Application No. PCT/CN2009/000050, filed on Jan. 14, 2009, which claims priority to foreign Patent Application No. CN 2008 10033348.5, filed on Jan. 31, 2008, the disclosures of which are incorporated herein by reference in their entirety.

TECHNICAL FIELD

The present invention relates to pharmaceutical chemistry field, and more particularly, relates to the use of cucurbitane triterpenoids extracted from *Momordica charantia* L. and pharmaceutical compositions thereof for prevention and treatment of diabetes and obesity.

BACKGROUND OF THE ART

At present, there are more than 150 millions people suffering from diabetes worldwide and it is expected that this figure will be over 300 millions by 2025. Among them, predominant are the patients suffering from type 2 diabetes (T2D). Since insulin resistance is the main metabolic abnormality of T2D, there is of considerable interest in the development of insulin-sensitizing agents, which treat diabetes by improving insulin resistance. Two major pathways have been targeted by clinical medications to ameliorate insulin resistance: peroxidsome-proliferator-activating receptors (PPARs) and AMP-activating receptors (AMPK). Thiazolidinediones (TZDs) and biguanides are the two most generally used agents for treating diabetes at present. TZDs are widely used but can result in many adverse effects, such as weight gain, fluid retention and heart failure. The dimethyl biguanide does not result in weight gain, but mainly acts in liver rather than muscles, and thus is not a satisfied therapy for treating diabetes. Therefore, there is a worldwide search for a better insulin-sensitizing agent for the treatment of diabetes.

Now, there are over one billion overweight adults. Among them, 300 millions are suffering from obesity, and this figure tends to increase quickly, resulting in a rapid increase in obesity-related diseases, such as type 2 diabetes, cardiac diseases, stroke and hypertension. The major reasons resulting in overweight and obesity are attributed to high fatty and high calorie diet, lack of exercise and the accelerating urbanization. There are only two marketed anti-obesity drugs that can be used in a long term: one is orlistat, a specific inhibitor of gastrointestinal tract lipases, but has very common gastrointestinal-related adverse effects; the other is sibutramine, a monoamine reuptake inhibitor, but it may increase blood pressure and heart rate. So there is an unmet need to develop safe and effective weight loss drugs.

*Momordica charantia* L. belongs to the family Cucurbitaceae and it has been widely used in China for more than 7 hundred years as a medicinal remedy for dispelling "heat", detoxicating, improving acuity of vision, invigorating stomach, relieving thirst, stopping diarrhea and as a helminthicide. The major chemical constituents in *Momordica charantia* L. include triterpenoid saponins, cerebrosides and polypeptides. Although several reports in the literature have described a hypoglycemic effect of *Momordica charantia L* extracts, it is not known whether cucurbitane triterpenoids isolated from *Momordica charantia L* have similar effects to reduce hyperglycaemia. Harinantenaina et al. (Chem. Pharm. Bull 54:1017-1021, 2006) has reported that triterpene-5β, 19-epoxy-3β,25-dihydroxycucurbita-6,23(E)-diene and 3β,7β,25-trihydroxycucurbita-5,23 (E)-dien-19-al isolated from *Momordica charantia* L. showed hypoglycemic effect on alloxan-induced diabetic mice at a dose of 400 mg/kg but the effect they reported was very mild. Moreover, there is no report to indicate that these compounds can stimulate the glucose uptake in muscle and adipose cells, promote the translocation of the glucose transporter 4 (GLUT4) to the cell membrane, increase the activity of adenosine monophosphate activated protein kinase (AMPK) and thus can be used for prevention and treatment of diabetes and obesity.

SUMMARY OF THE INVENTION

The object of the present invention is to provide a use of cucurbitane triterpenoids represented by the following formula isolated from *Momordica charantia* L. and pharmaceutical compositions thereof in the manufacture of drugs for prevention and treatment of diabetes and obesity. More particularly, these compounds have the functions of stimulating the glucose uptake in muscle and adipose cells, promoting the translocation of glucose transporter 4 (GLUT4) to the cell membrane and increasing the activity of adenosine monophosphate-activated protein kinase (AMPK), and thus may have the potential for prevention and treatment of diabetes and obesity. So the cucurbitane triterpenoids isolated from *Momordica charantia* L. and pharmaceutical compositions thereof may be acted as a glucose uptake stimulator, an agonist for the translocation of glucose transporter 4 (GLUT4) to the cell membrane, and an activator of adenosine monophosphate-activated protein kinase (AMPK) in muscle and adipose cells.

The present invention provides cucurbitane triterpenoids isolated from *Momordica charantia* L. and showing the activity of preventing and treating diabetes and obesity, which are represented by the following formula I:

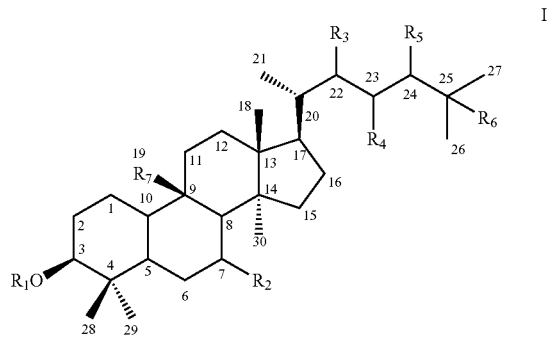

wherein $R_1$ is β-D-glucopyranosyl(1→6)-β-D-glucopyranosyl; $R_2$ is hydrogen; $R_3$, $R_4$, $R_5$ and $R_6$ are each a hydroxyl group; $R_7$ is methyl; and C5 forms a double bond together with C6; C22, C23 and C24 are chiral carbon atoms with S-, S- and R-configuration, respectively; or $R_1$ is β-D-xylopyranosyl(1→4)-[β-D-glucopyranosyl (1→6)]-β-D-glucopyranosyl; $R_2$ is hydrogen; $R_3$, $R_4$, $R_5$ and $R_6$ are each a hydroxyl group; $R_7$ is methyl; C5 forms a double bond together with C6; and C22, C23 and C24 are chiral carbon atoms with S-, S- and R-configuration respectively; or $R_2$ and $R_6$ are a hydroxyl group, respectively; $R_1$, $R_3$, $R_4$ and $R_5$ are each hydrogen; $R_7$ is an aldehyde group; C5 and C6, and C23 and C24 form a double bond, respectively; or $R_1$ is hydrogen; $R_2$ is hydrogen; $R_3$, $R_4$, $R_5$ and $R_6$ are each a hydroxyl group; $R_7$ is methyl; C5 forms a double bond together with C6; and C22, C23 and C24 are chiral carbon atoms with S-, S- and R-configuration respectively.

The present invention provides pharmaceutical compositions having the activity of preventing and treating diabetes and obesity, which is characterized in that the composition contains one or more of the cucurbitane triterpenoids isolated from *Momordica charantia* L. in a therapeutically effective amount and pharmaceutically acceptable adjuvants. The pharmaceutically acceptable adjuvants include, but not limited to, fillers, excipients well known in the art.

DETAILED DESCRIPTION OF THE INVENTION

Figure 1:
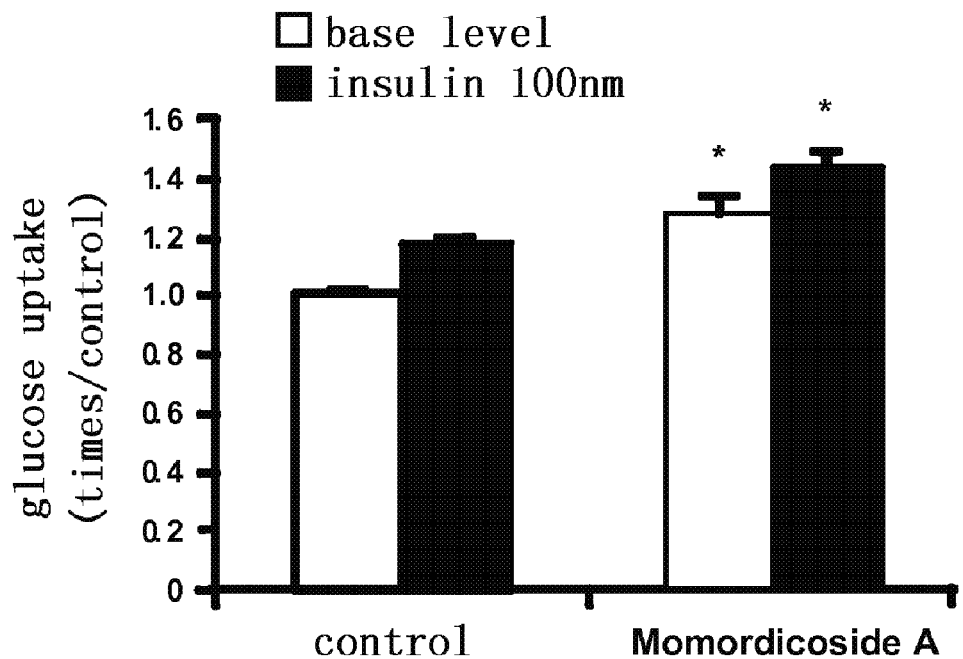
FIG. 1 shows the effect of momordicoside A on the glucose uptake in L6 muscle cells.

The present invention will be further described in detail with reference to the following examples and drawings, which should not be construed as the limitation for the invention.

I. SUMMARY

The present invention provides a use of cucurbitane triterpenoids isolated from *Momordica charantia* L. and pharmaceutical compositions thereof in the manufacture of drugs for prevention and treatment of diabetes and obesity.

The activity of prevention and treatment of diabetes and obesity in the invention refers to the ability to stimulate glucose uptake in muscle and adipose cells, promote the translocation of the glucose transporter 4 (GLUT4) to the cell membrane and increase the activity of adenosine monophosphate-activated protein kinase (AMPK)

II. COMPOUNDS

The present invention provides cucurbitane triterpenoids isolated from *Momordica charantia* L. and showing the activity of preventing and treating diabetes and obesity, which are represented by the following formula I:

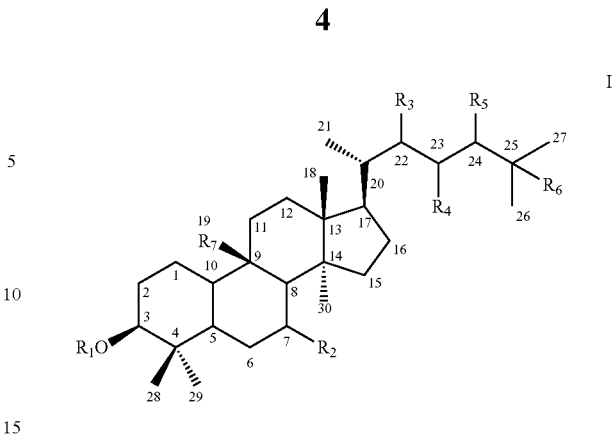

wherein $R_1$ is β-D-glucopyranosyl(1→6)-β-D-glucopyranosyl; $R_2$ is hydrogen; $R_3$, $R_4$, $R_5$ and $R_6$ are each a hydroxyl group; $R_7$ is methyl; C5 forms a double bond together with C6; and C22, C23 and C24 are chiral carbon atoms with S-, S- and R-configuration, respectively; or $R_1$ is β-D-xylopyranosyl(1→4)-[β-D-glucopyranosyl(1→6)]-β-D-glucopyranosyl; $R_2$ is hydrogen; $R_3$, $R_4$, $R_5$ and $R_6$ are each a hydroxyl group; $R_7$ is methyl; C5 forms a double bond together with C6; and C22, C23 and C24 are chiral carbon atoms with S-, S- and R-configuration, respectively; or $R_2$ and $R_6$ are a hydroxyl group, respectively; $R_1$, $R_3$, $R_4$ and $R_5$ are each hydrogen; $R_7$ is an aldehyde group; C5 and C6, and C23 and C24 form a double bond, respectively; or $R_1$ is hydrogen; $R_2$ is hydrogen; $R_3$, $R_4$, $R_5$ and $R_6$ are each a hydroxyl group; $R_7$ is methyl; C5 forms a double bond together with C6; and C22, C23 and C24 are chiral carbon atoms with S-, S- and R-configuration, respectively.

Specifically, these compounds include momordicoside A, momordicoside B, trihydroxycucurbita-5,23(E)-dien-19-al and 22(S),23(R),24(R),25-tetrahydroxycucurbita-5-ene, which are represented by the following formula, respectively:

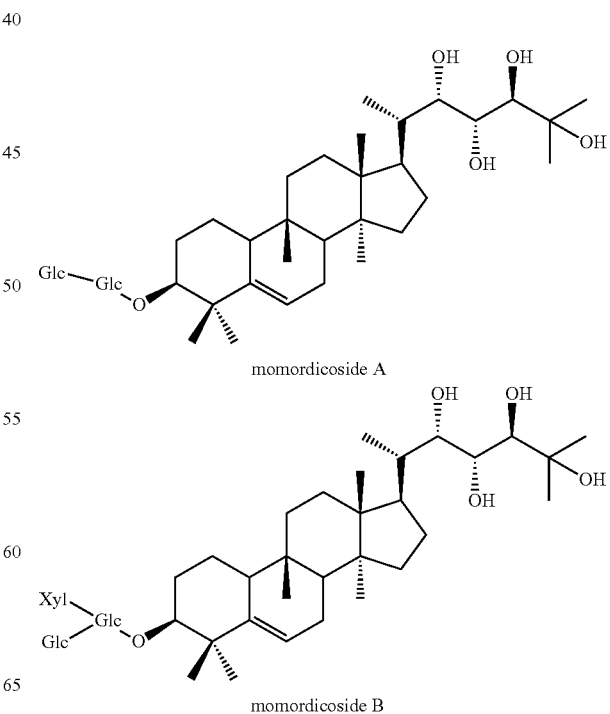

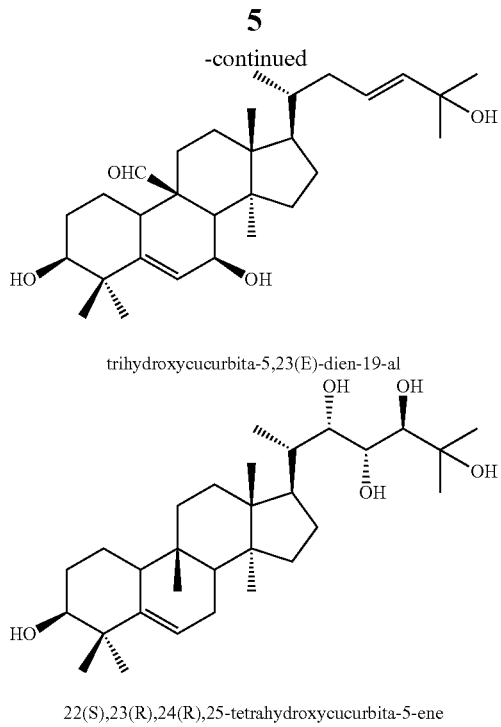

trihydroxycucurbita-5,23(E)-dien-19-al

22(S),23(R),24(R),25-tetrahydroxycucurbita-5-ene

EXAMPLES

Thin-layer chromatography (TLC) silica gel plate and silica gel (~300 mesh) used in column chromatography are manufactured by Qingdao Haiyang Chemical Group Corporation. The TLC spots were stained by spraying a solution of sulphuric acid-vanillin in ethanol.

Unless otherwise specified, all the ratios of related solvents herein are volume ratios.

Example 1

The Preparation of the Compounds 850 kg of fresh *Momordica charantia* L. was lyophilized to afford 85 kg of dry product, which was then pulverized and macerated in a 90% ethanol aqueous solution (volume ratio) at room temperature three times, each for three days, wherein the amount of the ethanol aqueous solution is 10 times of the weight of the raw material. The three ethanol solutions obtained from the above extraction were combined, and concentrated under reduced pressure to yield a total ethanol extract. After the total ethanol extract was diluted with water (50 L), the diluted solution was partitioned with dichloromethane (20 L) to give a dichloromethane extract and an aqueous solution. Then the aqueous solution was partitioned with n-butanol (20 L) to provide 800 g of n-butanol extract. The 800 g n-butanol extract was mixed with 500 g of AB-8 type macroporous resin (manufactured by Tianjin Gelatine Plant), and the resin mixed with the sample was put on a chromatographic column loaded with 3 kg of AB-8 resin, and eluted with 12 L of pure water, 30% ethanol (volume ratio) and 95% ethanol (volume ratio) respectively to afford 600 g of KG6, 60 g of KG7 and 80 g of KG8 respectively.

80 g of KG8 was subjected to a silica gel (2 kg, 100-200 mesh) column chromatography eluting successively with a subnatant liquid (each 10 L) of chloroform-methanol-water at a volume ratio of 40:3:1, 20:3:1, 10:3:1 and 65:35:10 respectively. Each 500 ml elute was collected as one fraction, and tested on a TLC plate, wherein a mixture of chloroform-methanol (v/v=10/1, 6/1 or 4/1) or a subnatant liquid of chloroform-methanol-water (v/v/v=10/3/1 or 65/35/10) was used as an eluent and 5% sulphuric acid-vanillin was used as a staining agent. According to the TLC plate, the similar fractions were combined and concentrated. The fractions with a Rf of 0.3-0.4 (effluent: chloroform-methanol with a ratio of 9:1) were combined to afford component 1 and the fractions with a Rf of 0.3-0.4 (eluent: subnatant liquid of chloroform-methanol-water with a ratio of 10:3:1) were combined to afford component 8.

The above component 1 was subjected to a silica gel column chromatography eluting with 1000 ml of chloroform-methanol (v/v=20/1). Each 20 ml elute was collected as one fraction, and tested on a TLC plate, wherein the eluent was chloroform-methanol (v/v=10/1), and the staining agent was 5% sulphuric acid-vanillin. The eluates, which showed a spot with a Rf of about 0.4 on the TLC plate, were combined and concentrated to afford 120 mg of trihydroxycucurbita-5,23(E)-dien-19-al.

The above component 8 was subjected to a MCI column chromatography with gradient elution (1000 ml of 30%-70% methanol aqueous solution). The obtained 40% fraction were subjected to a RP-18 column chromatography with gradient elution (500 ml of 30%-60% methanol aqueous solution). Each 20 ml was collected as one fraction, and tested on a TLC plate, wherein the eluent was the subnatant liquid of chloroform-methanol-water (v/v/v=8/3/1) and the staining agent was 5% sulphuric acid-vanillin. The elutes, which showed a spot with a Rf of about 0.3 or 0.4 on the TLC plate, were combined and concentrated to afford 250 mg of momordicoside A and 300 mg of momordicoside B, respectively.

40 mg of momordicoside A was treated with 0.1 M acetic acid aqueous solution for 7 days at 37° C. The resulted product was subjected to a preparative thin-layer chromatography eluting with chloroform-methanol (v/v=5/1). The eluates with a Rf of around 0.5-0.6 were combined and concentrated to afford 10 mg of 22(S),23(R),24(R),25-tetrahydroxycucurbita-5-ene.

Experimental Example 1

Testing the effect of momordicoside A on the glucose uptake in L6 muscle cells (FIG. 1)

After L6 cells were differentiated to myotube completely, they were incubated in serum-free DMEM containing 0.5% BSA for 16 hours. Then momordicoside A (final concentration 50 μM) was added therein to treat the cells for 1 hour and 20 minutes, while DMSO with the same volume was added into the blank control group. After that, they were washed with 1×PBS preheated at 37° C. twice, and 0.5% BSA Krebs buffer (NaCl 140 mM, KCl 5 mM, $MgSO_4$ 2.5 mM, $CaCl_2$ 1 mM, HEPES 20 mM, pH7.4) without or with insulin (final concentration 100 nM), followed by incubation at 37° C. for 40 minutes. A 2-[1,2-3H(N)]-deoxy-D-glucose solution (final concentration 0.5 μCi/ml) was added therein and incubated for 10 minutes at 37° C. Then the reaction was terminated by washing three times with ice-cold 1×PBS and 0.15 ml of 0.1% Triton was added therein for the lysis of the cells the counting in a liquid-scintillation counter. After the CPM value was corrected with the protein amount, the glucose uptake amount of L6 cells was calculated.

The results showed that the glucose uptake in L6 cells was increased significantly both at base level and under the stimulus of insulin after treated with 10 μM momordicoside A for 2 hours (FIG. 1). The data are shown in mean±standard error (X±SE) (n=3). The significance was shown as *p<0.05 compared with control groups under corresponding conditions.

Experimental Example 2

Figure 2:
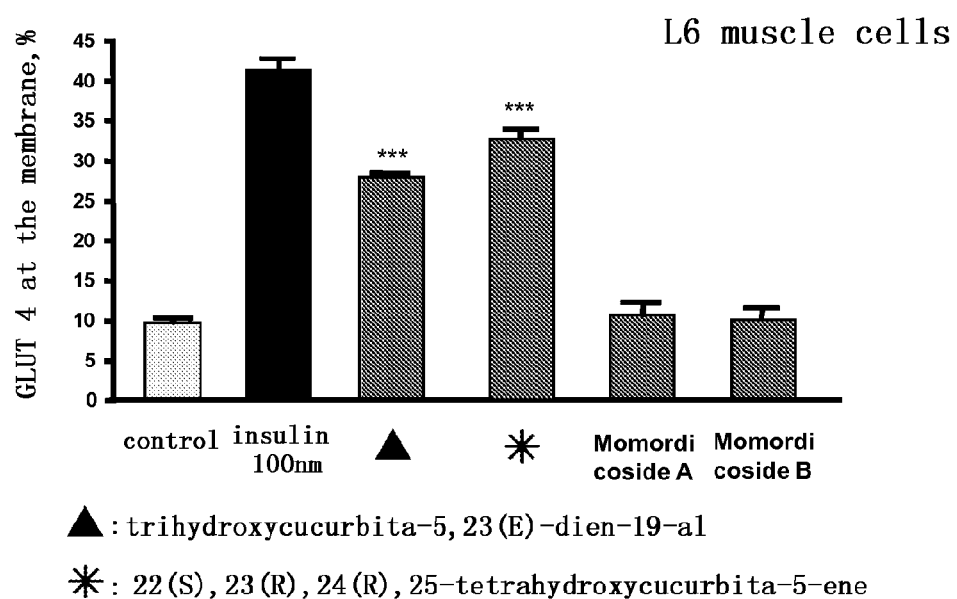
FIG. 2 shows the effects of various compounds on the translocation of glucose transporter 4 (GLUT4) to the cell membrane.

Effects of isolated compounds on the translocation of glucose transporter 4 (GLUT4) from cytosol to the cell membrane (FIG. 2)

After L6 cells were differentiated to myotube completely, they were treated for 2 hours with various test compounds, namely trihydroxycucurbita-5,23(E)-dien-19-al, 22(S),23(R),24(R),25-tetrahydroxycucurbita-5-ene, momordicoside A, momordicoside B (final concentration 10 μM, each) or 100 nM insulin (as positive control). The data were expressed as mean±standard error (X±SE) (n=3-4). The significance was shown as ***p<0.001 compared with solvent control groups. The results showed that trihydroxycucurbita-5,23(E)-dien-19-al and 22(S),23(R),24(R),25-tetrahydroxycucurbita-5-ene were capable of promoting the translocation of glucose transporter 4 (GLUT4) to the cell membrane, and hence increase the glucose uptake in cells.

Experimental Example 3

Figure 3:
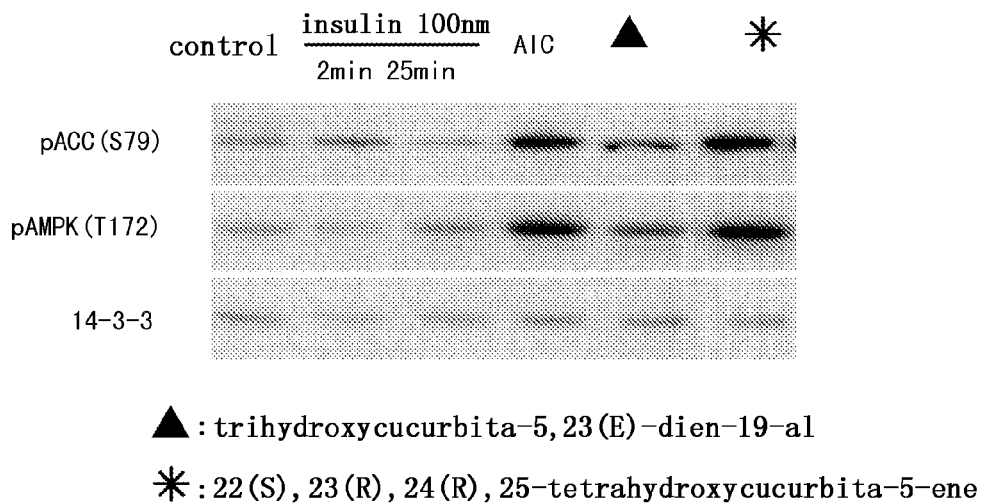
FIG. 3 shows the effects of trihydroxycucurbita-5,23(E)-dien-19-al and 22(S),23(R), 24(R),25-tetrahydroxycucurbita-5-ene on the activity of adenosine monophosphate-activated protein kinase (AMPK)

Testing the activities of trihydroxycucurbita-5,23(E)-diene-19-aldehyde and 22(S), 23(R),24(R),25-tetrahydroxy cucurbita-5-ene on adenosine monophosphate-activated protein kinase (AMPK) (FIG. 3)

3T3-L1 adipose cells was incubated for 60 minutes in a medium containing 10 μM compounds, or in a medium containing 2 mM 5-amino4-imidazolecarboxamide nucleotide (AIC, positive control) or DMSO as a solvent control, followed by being treated with 100 nM insulin for 2 minutes or 25 minutes. Then the proteins pACC and pAMPK in cell lysate were determined with corresponding antibodies. The total amount of protein 14-3-3 was used as the quality control for sample loading. The results showed that trihydroxycucurbita-5,23 (E)-dien-19-al and 22(S),23(R),24(R),25-tetrahydroxycucurbita-5-ene were capable of activating the AMPK signaling pathway significantly, and thus might be useful for the treatment of diabetes and obesity.

Experimental Example 4

Figure 4:
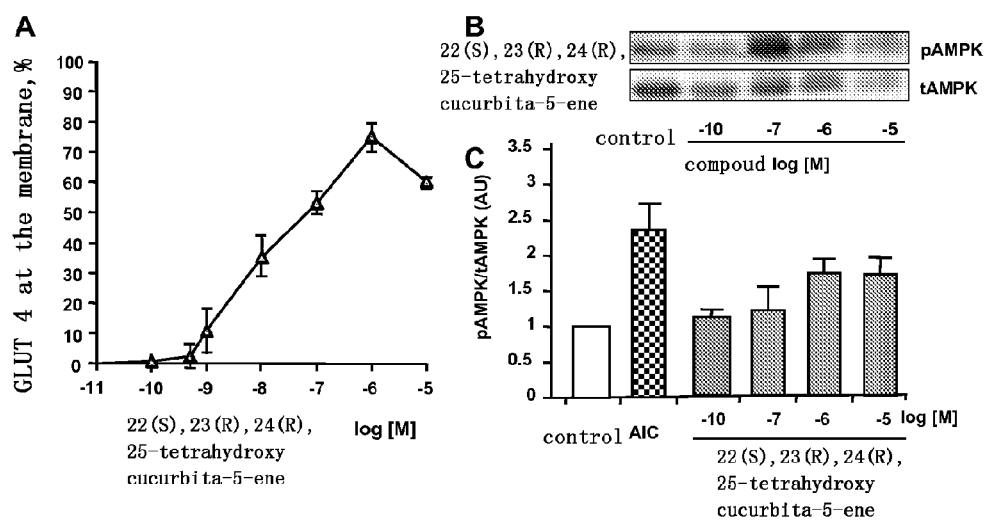
FIG. 4 shows the dose dependency of 22(S),23(R),24(R), 25-tetrahydroxycucurbita-5-ene on the translocation of glucose transporter 4 (GLUT4) to the cell membrane and the AMPK phosphorylation in 3T3-L1 adipose cells.

Dose-dependent effect of 22(S),23(R),24(R),25-tetrahydroxycucurbita-5-ene on GLUT4 translocation and the phosphorylation of AMPK in 3T3-L1 adipose cells (FIG. 4)

According the processes in experimental examples 2 and 3, 22(S),23(R),24(R),25-tetrahydroxycucurbita-5-ene was tested at different concentrations ($10^{-10}$, $10^{-7}$, $10^{-6}$, $10^{-5}$ M). The results were shown in FIG. 4, wherein A was the dose dependency curve regarding the effect on translocation of glucose transporter 4 (GLUT4); B showed the effect of the compound at different concentrations on the activity of adenosine monophosphate-activated protein kinase (AMPK) in 3T3-L1 adipose cells; C showed the quantification of the ratio of phosphorylated adenosine monophosphate-activated protein kinase (pAMPK) to total adenosine monophosphate-activated protein kinase (tAMPK) at different concentrations of the compound in 3T3-L1 adipose cells. The experimental results showed that the effect of 22(S), 23 (R), 24(R),25-tetrahydroxycucurbita-5-ene on the translocation of glucose transporter 4 (GLUT4) to the cell membrane is significantly related to the phosphorylation of AMPK (namely, the activation of the AMPK signaling pathway), and the maximal effects was reached at the concentration of $10^{-6}$M.

Experimental Example 5

Testing the effects of 22(S),23(R),24(R),25-tetrahydroxycucurbita-5-ene on the insulin signaling pathway (namely monophosphoinositide 3-kinase/protein kinase B(PI-3K/Akt) pathway) in 3T3-L1 adipose cells and L6 muscle cells.

A. 10 μM 22(S),23(R),24(R),25-tetrahydroxycucurbita-5-ene or 100 nM insulin (positive control) was added in the differentiated 3T3-L1 adipose cells using DMSO (final concentration of DMSO: 0.2%) as a solvent with or without wortmanin (an inhibitor of monophosphoinositide 3-kinase), and the activity on GLUT4 translocation was determined as described in experimental example 2. The data were expressed in mean±standard error (X±SE). The significances were shown as *p<0.05 and **p<0.01 compared with the solvent control groups. The results showed that wortmanin, the inhibitor of PI3-kinase, did not affect the activity of 22(S), 23(R),24(R),25-tetrahydroxycucurbita-5-ene on GLUT4 translocation, indicating that the effect of 22(S),23(R),24(R), 25-tetrahydroxycucurbita-5-ene on GLUT4 translocation is independent of this insulin signaling pathway (FIG. 5).

B. 3T3-L1 adipose cells and L6 muscle cells were incubated for 30 minutes in a medium containing 10 μM trihydroxycucurbita-5,23(E)-dien-19-al or 22(S),23(R),24(R),25-tetrahydroxycucurbita-5-ene, or a medium containing 100 nM insulin (positive control) or DMSO as a solvent control. The phosphorylation of protein kinase B [Akt (S473)] and the total protein kinase B (14-3-3) were determined with corresponding antibodies. The significances are shown as *p<0.05 and **p<0.01 compared with the solvent control groups. The results showed that trihydroxycucurbita-5,23(E)-dien-19-al and 22(S), 23(R),24(R),25-tetrahydroxycucurbita-5-ene were not able to increase the phosphorylation of protein kinase B, indicating that trihydroxycucurbita-5,23(E)-dien-19-al and 22(S),23 (R), 24(R),25-tetrahydroxycucurbita-5-ene did not influence the insulin signaling pathway (FIG. 6).

Figure 5:
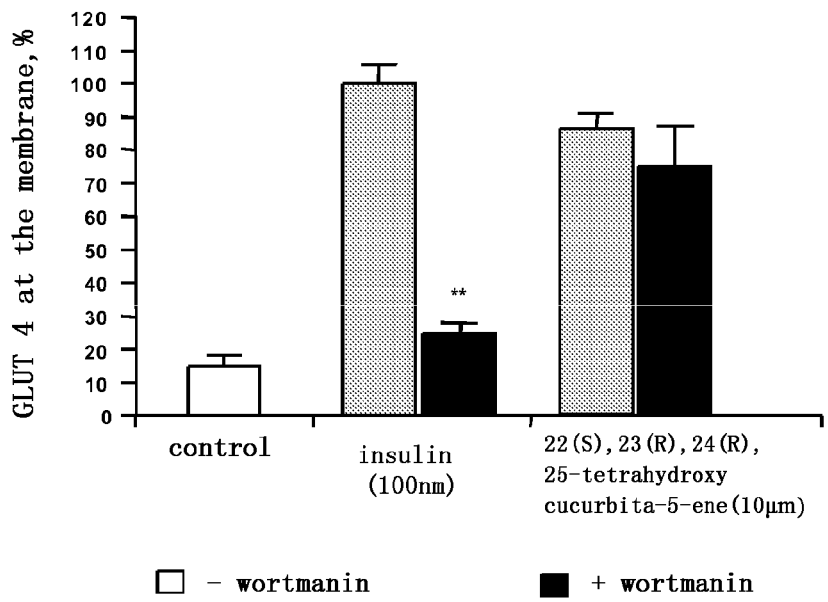
FIG. 5 shows the effect of 22(S),23(R),24(R),25-tetrahydroxycucurbita-5-ene on GLUT4 translocation under the condition that the PI3K/Akt insulin signaling pathway is inhibited.
Figure 6:
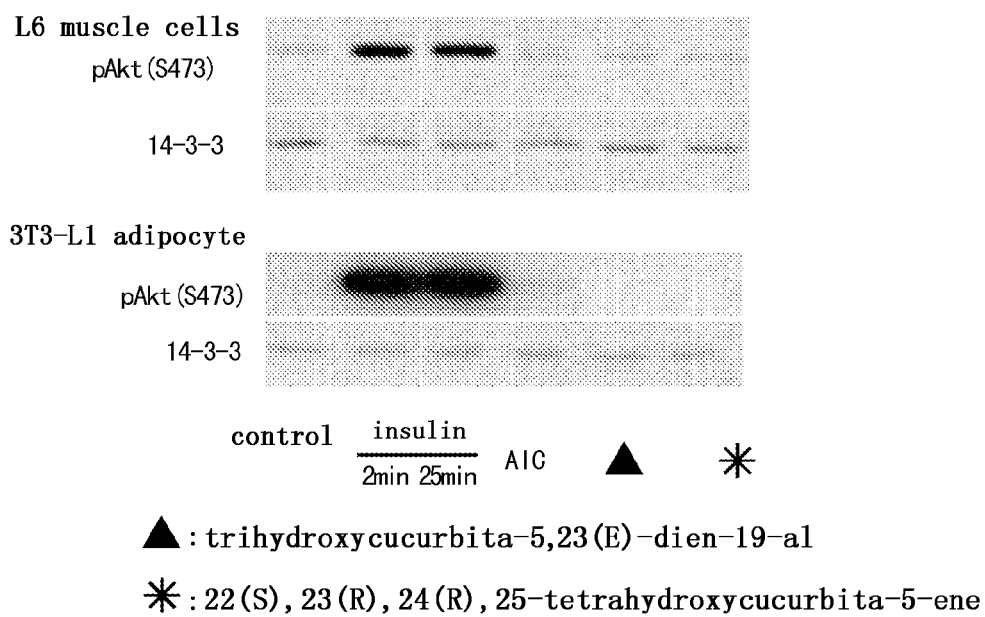
FIG. 6 shows the effects of trihydroxycucurbita-5,23(E)-dien-19-al and 22(S),23(R), 24(R),25-tetrahydroxycucurbita-5-ene on the activity of protein kinase B (Akt).

The insulin signaling pathway and AMPK signaling pathway are the two main signaling pathways to mediate GLUT4 translocation and glucose uptake, and the results in FIG. 5 and FIG. 6 were consistent with those in FIG. 3 and FIG. 4, which indicated that the compounds stimulate GLUT4 translocation and glucose uptake by the AMPK signaling pathway.

The invention claimed is:

1. A method of activating adenosine monophosphate-activated protein kinase comprising administering a therapeutically effective amount of an isolated and purified cucurbitiane triterpenoid compound to a subject in need of treating at least one of diabetes or obesity, the cucurbitiane triterpenoid compound being selected from the group consisting of:

momordicoside A represented by the following formula:

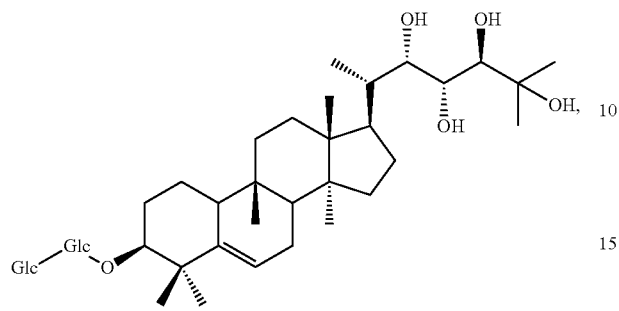

momordicoside B represented by the following formula:

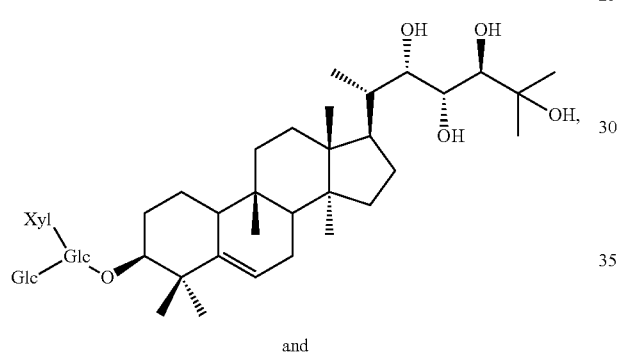

and

22(S),23(R),24(R),25tetrahydroxycucurbita-5-en represented by the following formula:

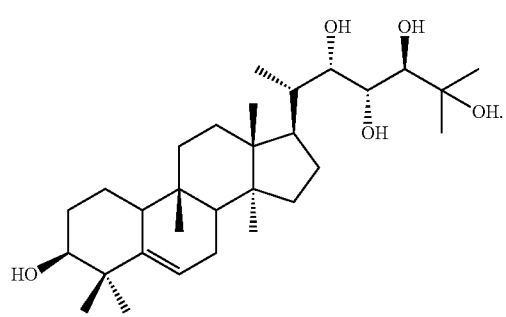

2. A method of treating adenosine monophosphate-activated protein kinase related diseases comprising administering a therapeutically effective amount of an isolated and purified cucurbitiane triterpenoid compound to a subject with such disease, wherein the adenosine monophosphate-activated protein kinase related diseases are selected from the group consisting of diabetes and obesity, the cucurbitiane triterpenoid compound being selected from the group consisting of:

momordicoside A represented by the following formula:

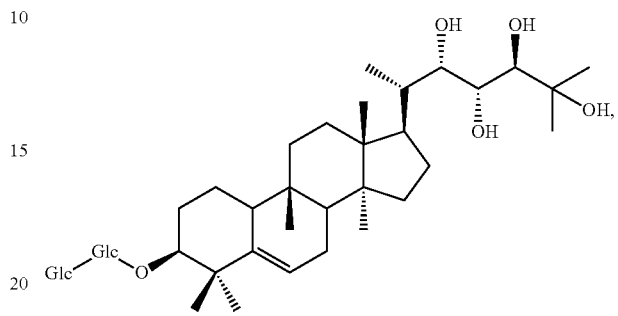

momordicoside B represented by the following formula:

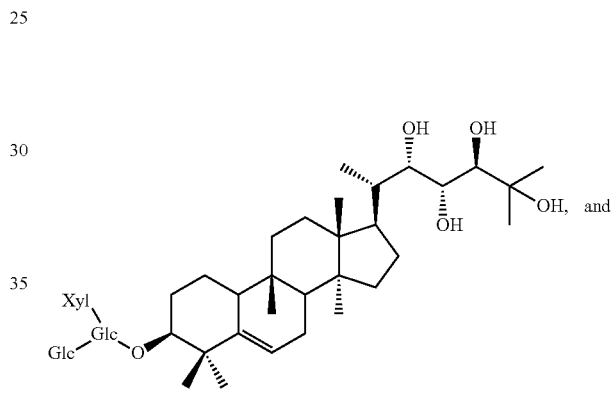

and

22(S),23(R),24(R),25tetrahydroxycucurbita-5-en represented by the following formula:

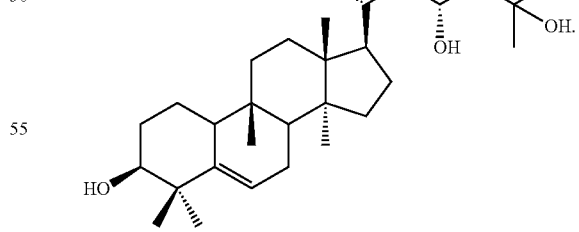

3. A method of activating adenosine monophosphate-activated protein kinase comprising administering a therapeutically effective amount of a purified compound isolated from *Momordica charantia* L. to a subject having a disease selected from the group consisting of diabetes and obesity, the compound having a representative formula I:

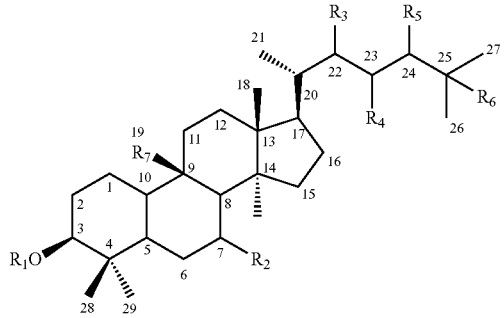

wherein $R_1$ is β-D-glucopyranosyl(1→6)-β-D-glucopyranosyl; $R_2$ is hydrogen; $R_3$, $R_4$, $R_5$ and $R_6$ are each a hydroxyl group; $R_7$ is methyl; C5 forms a double bond together with C6; and C22, C23 and C24 are chiral carbon atoms with S-, S- and R-configuration, respectively; or $R_1$ is β-D-xylopyranosyl(1→4)-[β-D-glucopyranosyl(1→6)]β-D-glucopyranosyl; $R_2$ is hydrogen; $R_3$, $R_4$, $R_5$ and $R_6$ are each a hydroxyl group; $R_7$ is methyl; C5 forms a double bond together with C6; and C22, C23 and C24 are chiral carbon atoms with S-, S- and R-configuration, respectively; or $R_2$ and $R_6$ are a hydroxyl group, respectively; $R_1$, $R_3$, $R_4$ and $R_5$ are each hydrogen; $R_7$ is a methyl groop; C5 and C6, and C23 and C24 form a double bond, respectively; or $R_1$ is hydrogen; $R_2$ is hydrogen; $R_3$, $R_4$, $R_5$ and $R_6$ are each a hydroxyl group; $R_7$ is methyl; C5 forms a double bond together with C6; and C22, C23 and C24 are chiral carbon atoms with S-, S- and R-configuration, respectively.

4. A method of promoting the translocation of glucose transporter 4 to a cell membrane comprising administering a therapeutically effective amount of an isolated and purified cucurbitane triterpenoid compound to a subject having a disease selected from the group consisting of diabetes and obesity, the cucurbitane triterpenoid compound is selected from the group consisting of:

momordicoside A represented by the following formula:

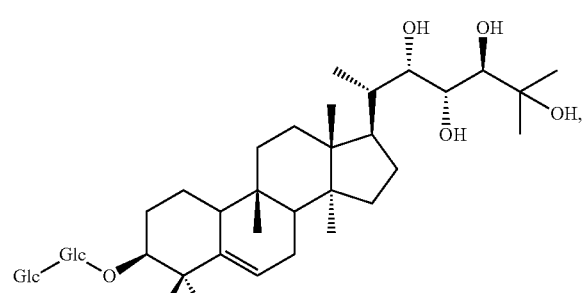

momordicoside B represented by the following formula:

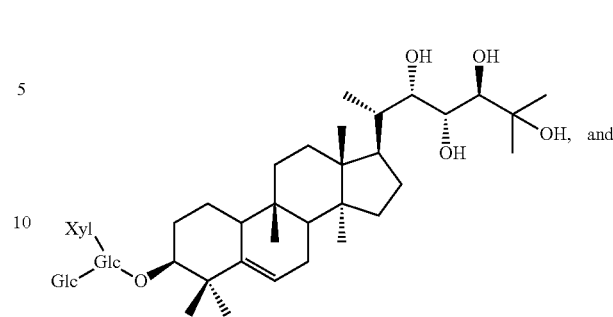

22(S),23(R),24(R),25tetrahydroxycucurbita-5-en represented by the following formula:

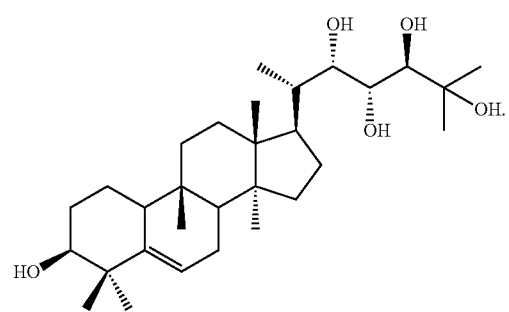

5. A method of treating diabetes and obesity comprising administering to a subject in need of such treatment an isolated and purified cucurbitane triterpenoid compound selected from the group consisting of:

momordicoside A represented by the following formula:

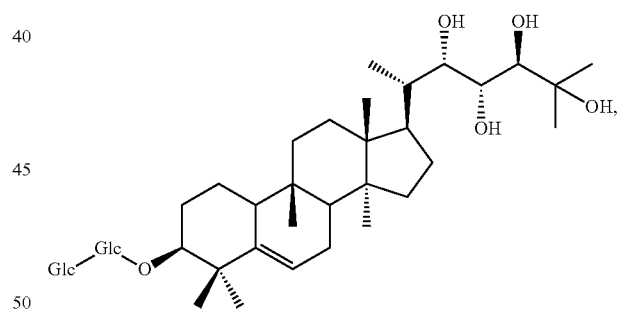

momordicoside B represented by the following formula:

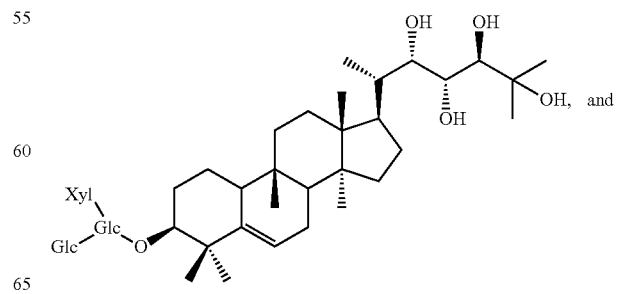

22(S),23(R),24(R),25tetrahydroxycucurbita-5-en represented by the following formula:
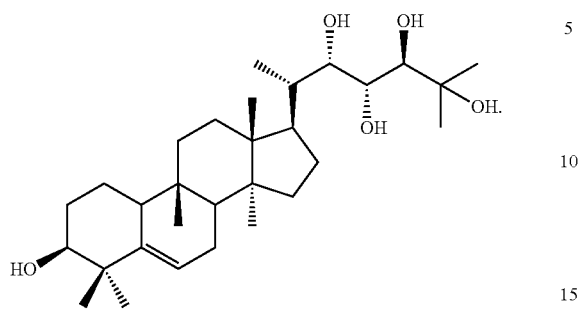
6. The method according to claim 5, wherein the cucurbitane triterpenoid compound acts as a glucose uptake stimulator, an agonist for translocation of glucose transporter 4 to a cell membrane, and an activator of adenosine monophosphate-activated protein kinase.
* * * * *

UNITED STATES PATENT AND TRADEMARK OFFICE
CERTIFICATE OF CORRECTION

PATENT NO. : 8,722,634 B2
APPLICATION NO. : 12/865843
DATED : May 13, 2014
INVENTOR(S) : Ye et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 137 days.

Signed and Sealed this
Twenty-ninth Day of September, 2015

Michelle K. Lee
*Director of the United States Patent and Trademark Office*